US009326933B2

(12) United States Patent
Prosise et al.

(10) Patent No.: US 9,326,933 B2
(45) Date of Patent: May 3, 2016

(54) ORAL CARE COMPOSITIONS

(75) Inventors: William Prosise, Ramsey, NJ (US); Jay Hilsenbeck, Atlanta, GA (US)

(73) Assignee: ISP INVESTMENTS INC., Wilmington, DE (US)

( * ) Notice: Subject to any disclaimer, the term of this patent is extended or adjusted under 35 U.S.C. 154(b) by 1934 days.

(21) Appl. No.: 12/373,363

(22) PCT Filed: Jul. 26, 2007

(86) PCT No.: PCT/US2007/074424
§ 371 (c)(1),
(2), (4) Date: Jul. 27, 2009

(87) PCT Pub. No.: WO2008/014375
PCT Pub. Date: Jan. 31, 2008

(65) Prior Publication Data
US 2010/0034755 A1    Feb. 11, 2010

Related U.S. Application Data

(60) Provisional application No. 60/833,517, filed on Jul. 26, 2006.

(51) Int. Cl.
*A61K 8/36* (2006.01)
*A61K 8/86* (2006.01)
*A61Q 11/00* (2006.01)

(52) U.S. Cl.
CPC .. *A61K 8/86* (2013.01); *A61Q 11/00* (2013.01)

(58) Field of Classification Search
USPC .............................. 260/33.6; 523/113; 424/49
See application file for complete search history.

(56) References Cited

U.S. PATENT DOCUMENTS 3,003,988 A * 10/1961 Germann et al. ............. 524/474
6,692,725 B2    2/2004 Endo
2001/0056133 A1 * 12/2001 Montgomery et al. ....... 523/113

OTHER PUBLICATIONS

Borealisgroup, "Polymer Dictionary". Copyright 2010. printed Aug. 7, 2012; two (2) pages.*

* cited by examiner

*Primary Examiner* — Walter Webb
(74) *Attorney, Agent, or Firm* — Thompson Hine LLP; William J. Davis

(57) ABSTRACT

In accordance with this invention, there is provided an oral care composition comprising a multimodal blend of copolymers of maleic acid or maleic anhydride and an alkyl vinyl ether and a non-cationic antibacterial agent. The compositions feature improved retention of the antibacterial agent on teeth.

12 Claims, 2 Drawing Sheets

ORAL CARE COMPOSITIONS

CROSS-REFERENCE TO RELATED APPLICATIONS

The present application claims the benefit of U.S. Provisional Application Ser. No. 60/833,517, filed on Jul. 26, 2006, the disclosure of which is hereby incorporated by reference in its entirety.

FIELD OF THE INVENTION

This invention relates to oral care compositions, such as toothpaste compositions, and more particularly, to such compositions containing a copolymer of maleic acid or maleic anhydride and an alkyl vinyl ether, e.g. Gantrez® S-97, blended with one or more copolymers of maleic acid or maleic anhydride and an alkyl vinyl ether of different specific viscosity and a non-cationic antibacterial agent e.g., triclosan. The compositions provide a high retention of the antibacterial agenet on teeth.

BACKGROUND OF THE INVENTION

Oral care compositions of non-cationic antibacterial enhancing agents and unimodal maleic acid or maleic anhydride copolymers or other polycarboxylates, e.g., methylvinyl ether-maleic acid anhydride, are well known in the art. See U.S. Pat. Nos. 6,692,725; 5,776,435; 5,686,064; 5,582,816; 5,538,715; 5,531,982; 5,334,375; 5,496,540; 5,472,685; 5,466,437; 5,453,265; 5,368,844; 5,356,615; 5,344,641; 5,312,618; 5,294,431; 5,292,526; 5,288,480; 5,279,813; 5,275,805; 5,273,741; 5,260,062; 5,256,401; 5,192,531; 5,192,530; 5,188,821; 5,180,578; 5,178,851; 5,167,951; 5,156,835; 5,135,738; 5,080,887; 5,037,637; 5,032,386; and 4,894,220.

However, it is desirable for improved dental health to provide oral care compositions with improved retention of an antibacterial enhancing agent on teeth. Accordingly, it is an object of this invention to improve the efficacy of oral care compositions containing a non-cationic antibacterial agent.

SUMMARY OF THE INVENTION

We have discovered that oral care compositions comprised of multimodal blends of copolymers of maleic acid or maleic anhydride and an alkyl vinyl ether and a non-cationic antibacterial agent exhibit unexpectedly high retention of the antibacterial agent on teeth.

In accordance with this invention, there is provided oral care compositions comprising a multimodal blend of copolymers of maleic acid or maleic anhydride and an alkyl vinyl ether and a non-cationic antibacterial agent. The oral care compositions exhibit unexpectedly high retention of the antibacterial agent on teeth.

In a preferred embodiment, the oral care composition comprises a bimodal blend of copolymers of maleic acid or maleic anhydride and an alkyl vinyl ether, the copolymers having specific viscosities in the ranges of 2-10 and 0.1-2 respectively and the copolymers being present in a weight ratio of 10.90 to 90:10.

In another embodiment, there is provided a method of improving retention of a non-cationic antibacterial agent on teeth, the method comprising delivering the non-cationic antibacterial agent to the teeth in combination with a multimodal blend of copolymers of maleic acid or maleic anhydride and an alkyl vinyl ether.

DETAILED DESCRIPTION OF THE INVENTION

Figure 1:
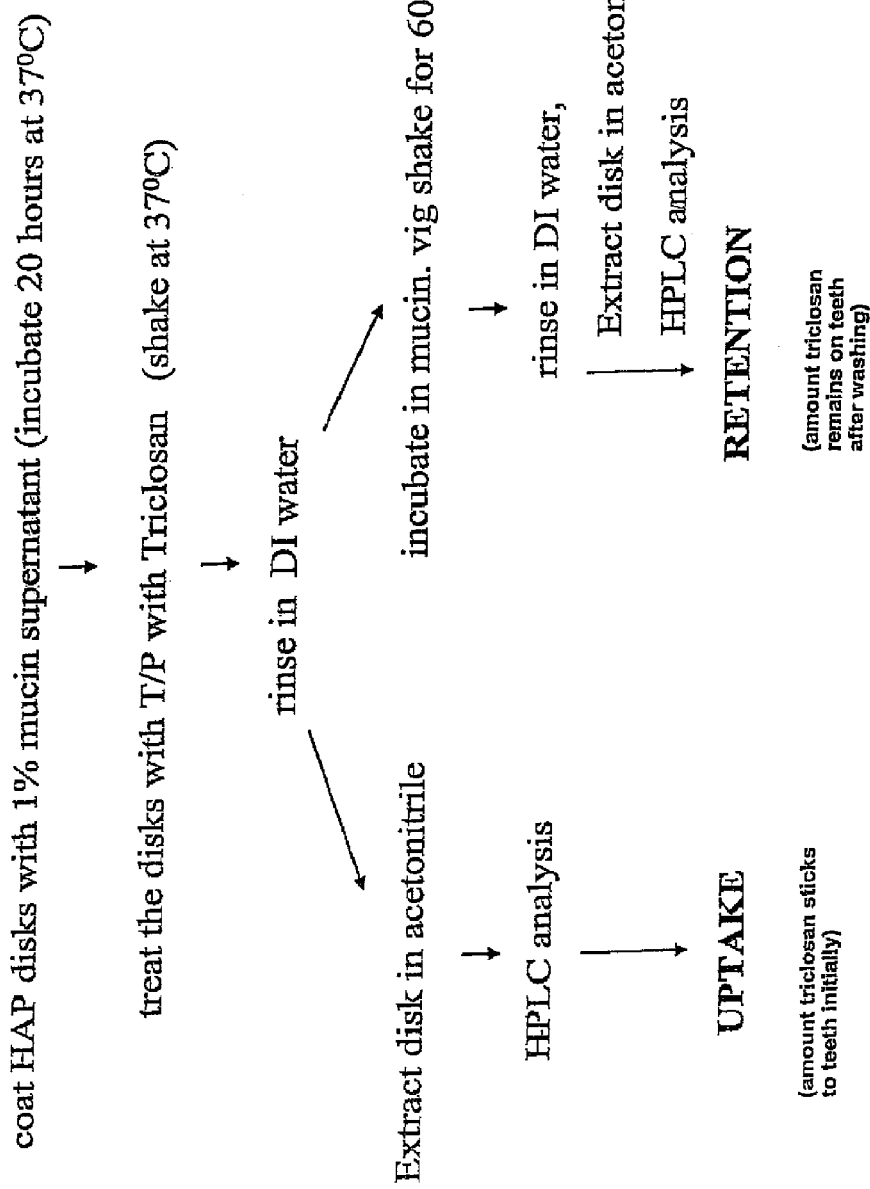
FIG. 1 shows the procedure used for testing the efficacy of uptake/retention of the non-cationic antibacterial agent triclosan on mucin-coated HAP disks.

While the invention is described hereinafter with respect to preferred embodiments thereof e.g., a bimodal distribution of maleic acid or maleic anhydride alkyl vinyl ether copolymers in combination with the non-cationic antibacterial agent triclosan, the invention can also be practiced in connection with any multimodal, e.g., trimodal distributions of maleic acid or maleic anhydride alkyl vinyl ether copolymers and other non-cationic antibacterial agents such as thymol, phenol and other phenolics.

As used herein, "specific viscosity" refers to the viscosity of the alkyl vinyl ether maleic anhydride copolymer in a suitable solvent divided by the viscosity of the solvent.

The oral care composition can take the form of any conventional oral care composition. In addition to toothpastes, the oral care composition can be in the form of a denture adhesive, a mouth wash, a lozenge, chewing gum and the like.

The non-cationic anti-bacterial agent can be present in an amount of about 0.01-5 wt %, preferably 0.1-4 wt % and more preferably 0.2-3 wt %.

The differing specific viscosities (SV) of the multimodal blends of maleic acid or maleic anhydride alkyl vinyl ether copolymers can be in the range of 0.1 to about 10. In the case of a bimodal blend of maleic acid or maleic anhydride alkyl vinyl ether copolymers, the differing specific viscosities can be in the ranges of 2-10 and 0.1-2 respectively, preferably 2-6 and 0.1-1.75 and more preferably 2-4 and 0.1-1.5.

The maleic acid or maleic anhydride alkyl vinyl ether copolymers can be present in a wt. ratio of 10:90 to 90:10, preferably 20:80 to 80:20 and more preferably 25:75 to 75:25.

The oral care compositions can contain up to about 10% by weight of the maleic acid or maleic anhydride alkyl vinyl ether copolymers. In toothpastes, the maleic acid or maleic anhydride alkyl vinyl ether copolymers can be present in an amount of 0.1-5% by weight, preferably 0.5-3%.

In a further embodiment, the invention can be practiced in conjunction with a surface active vegetable gum as described more fully in commonly assigned PCT International Application entitled "ORAL CARE COMPOSITIONS" filed on even date herewith, the disclosure of which is hereby incorporated by reference in its entirety.

The oral care composition of this invention can contain 0.001-5 wt % of a surface active vegetable gum such as gum arabic, hydroxypropylmethylcellulose or karaya gum.

In a particularly preferred embodiment, the non-cationic antibacterial agent is present in the presence of a known surface active agent such as sodium lauryl sulfate. Other surface active agents normally used in oral care compositions can also be used; an example is Poloxamers. A preferred is Poloxamer 407 available from BASF Corp.

Example

Model Toothpaste Mixtures for Triclosan Uptake and Retention

Stock Toothpaste (T/P) Mixture without Abrasive:
Add:
61.00 g Water
20.00 g 70% Sorbitol 13.00 g Propylene glycol
2.46 g Sodium lauryl sulfate
0.30 g Non-cationic antibacterial (triclosan)
1.00 g Ethanol
0.24 g NaF
2.00 g Maleic acid-methyl vinyl ether copolymer*

*suitably present in an amount of 0.01-5% by wt of the mixture.

TABLE

| BimodaL Mixtures of Copolymer Anhydride in Weight Percent | | | | |
|---|---|---|---|---|
| Copolymer | Percentage by Wt. | | | SV |
| (A) | 25 | 50 | 75 | 2-4 |
| (B) | 75 | 50 | 25 | 0.1-1.5 |

Figure 2:
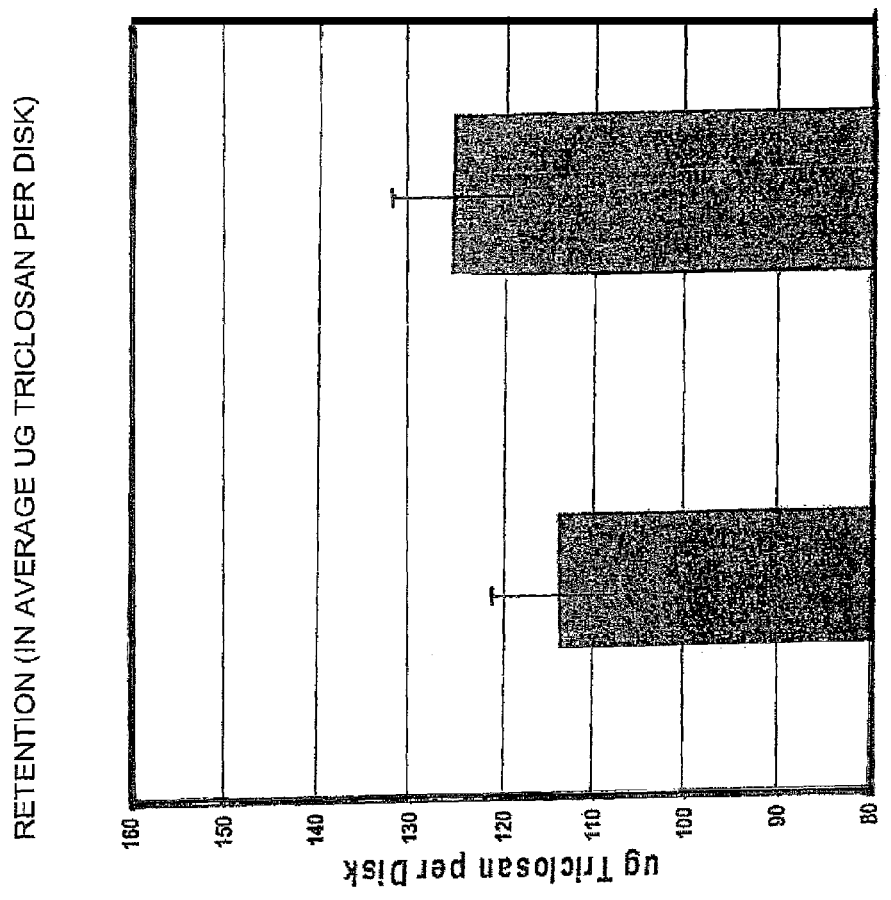
FIG. 2 is a graphical representation of retention of triclosan on disks treated with a composition containing a bimodal molecular weight maleic acid-methylvinyl ether copolymer (SV=2-4 and SV=0.1-1.5) vs. a control (unimodal molecular weight distribution copolymer).

The results in FIG. 2 show the improved efficacy of non-cationic antibacterial agent retention in accordance with this invention of the bimodal copolymer over the control unimodal copolymer.

What is claimed:

1. An oral care composition comprising:
   (a) a multimodal blend of copolymers of maleic acid or maleic anhydride and an alkyl vinyl ether; and
   (b) a non-cationic antibacterial agent.

2. The oral care composition of claim 1 wherein said multimodal blend is a bimodal blend.

3. The oral care composition of claim 2 wherein said bimodal blend of copolymers have specific viscosities in the ranges of 2-10 and 0.1-2 respectively.

4. The oral care composition of claim 3 wherein said bimodal blend of copolymers have specific viscosities in the ranges of 2-6 and 0.1-1.75 respectively.

5. The oral care composition of claim 4 wherein said bimodal blend of copolymers have specific viscosities in the ranges of 2-4 and 0.1-1.5 respectively.

6. The oral care composition of claim 1 wherein said non-cationic antibacterial agent is triclosan.

7. The oral care composition of claim 1 wherein said alkyl vinyl ether is methyl vinyl ether.

8. The oral care composition of claim 2 wherein said copolymers are present in a weight ratio of 10:90 to 90:10.

9. The oral care composition of claim 8 wherein said copolymers are present in a weight ratio of 20:80 to 80:20.

10. The oral care composition of claim 8 wherein said copolymers are present in a weight ratio of 20:80 to 80:20.

11. An oral care composition comprising
    (a) a bimodal blend of copolymers of maleic acid or maleic anhydride and an alkyl vinyl ether, said copolymers having specific viscosities in the ranges of 2-10 and 0.1-2 respectively and being present in a weight ratio of 10:90 to 90:10; and
    (b) a non-cationic antibacterial agent wherein said composition exhibits improved retention of said agent on teeth.

12. A method of improving retention of a non-cationic antibacterial agent on teeth, said method comprising delivering said non-cationic antibacterial agent to said teeth in combination with a multimodal blend of copolymers of maleic acid or maleic anhydride and an alkyl vinyl ether.

* * * * *